(12) United States Patent
Yamada (10) Patent No.: US 10,262,402 B2
(45) Date of Patent: Apr. 16, 2019

(54) CURVED LINE CORRECTION APPARATUS, METHOD, AND MEDIUM

(71) Applicant: FUJIFILM Corporation, Tokyo (JP)

(72) Inventor: Kenta Yamada, Tokyo (JP)

(73) Assignee: FUJIFILM Corporation, Minato-Ku, Tokyo (JP)

(*) Notice: Subject to any disclaimer, the term of this patent is extended or adjusted under 35 U.S.C. 154(b) by 145 days.

(21) Appl. No.: 14/804,794

(22) Filed: Jul. 21, 2015

(65) Prior Publication Data

US 2016/0035071 A1 Feb. 4, 2016

(30) Foreign Application Priority Data

Jul. 31, 2014 (JP) ................................. 2014-156625

(51) Int. Cl.
*G06T 7/12* (2017.01)
*G06T 5/20* (2006.01)
(Continued)

(52) U.S. Cl.
CPC ............... *G06T 5/20* (2013.01); *A61B 5/055* (2013.01); *A61B 6/032* (2013.01); *A61B 6/461* (2013.01);
(Continued)

(58) Field of Classification Search
CPC .................................................. G06T 11/203
See application file for complete search history.

(56) References Cited

U.S. PATENT DOCUMENTS

2006/0291726 A1* 12/2006 Takeshima ........... G06K 9/6206
382/209
2008/0062177 A1* 3/2008 Gaul ..................... G06T 11/203
345/440
(Continued)

FOREIGN PATENT DOCUMENTS

JP   2005-028051 A    2/2005
JP   2009279206 A    12/2009
(Continued)

OTHER PUBLICATIONS

Communication dated Nov. 22, 2016, from the Japanese Patent Office in counterpart application No. 2014-156625.
(Continued)

*Primary Examiner* — Jitesh Patel
(74) *Attorney, Agent, or Firm* — Sughrue Mion, PLLC (57) ABSTRACT

A curved line correction apparatus includes a correction target receiving unit that receives selection of a correction target point when an instruction mark is placed on an arbitrary point on a curved line composed of a plurality of arranged points, a correction target range setting unit that sets a certain range of the curved line, including the correction target point, as a correction target range, and a correction unit that corrects a portion of the curved line within the correction target range by moving the correction target point and a point within the correction target range when movement of the instruction mark is received, in which the correction target range setting unit changes the size of the correction target range when an instruction input to change the range is received with the instruction mark being placed on the correction target point.

16 Claims, 6 Drawing Sheets

(51) Int. Cl.
*A61B 5/055* (2006.01)
*A61B 6/03* (2006.01)
*A61B 6/00* (2006.01)
*G06K 9/46* (2006.01)
*G06T 7/00* (2017.01)
*G06F 3/0484* (2013.01)
*G06K 9/62* (2006.01)

(52) U.S. Cl.
CPC ............. *A61B 6/468* (2013.01); *A61B 6/469* (2013.01); *A61B 6/503* (2013.01); *A61B 6/5217* (2013.01); *G06F 3/04842* (2013.01); *G06F 3/04845* (2013.01); *G06K 9/46* (2013.01); *G06K 9/6254* (2013.01); *G06T 7/0012* (2013.01); *G06T 7/12* (2017.01); *A61B 2576/023* (2013.01); *G06K 2209/051* (2013.01); *G06T 2200/04* (2013.01); *G06T 2207/10072* (2013.01); *G06T 2207/10081* (2013.01); *G06T 2207/20096* (2013.01); *G06T 2207/20104* (2013.01); *G06T 2207/30048* (2013.01); *G06T 2210/41* (2013.01); *G06T 2211/40* (2013.01)

(56) References Cited

U.S. PATENT DOCUMENTS

| | | | | |
|---|---|---|---|---|
| 2008/0101682 A1* | 5/2008 | Blanford | ............... | G01B 11/005 382/141 |
| 2008/0189629 A1* | 8/2008 | Diederiks | ........... | G06F 3/04842 715/762 |
| 2008/0252660 A1* | 10/2008 | Masumoto | ............ | G06T 11/203 345/642 |
| 2009/0128486 A1* | 5/2009 | Nijlunsing | .......... | G06F 3/04845 345/157 |
| 2009/0290769 A1* | 11/2009 | Matsumoto | ........... | G06T 11/203 382/128 |
| 2009/0297031 A1* | 12/2009 | Pettigrew | ............... | G06K 9/342 382/195 |
| 2010/0215245 A1* | 8/2010 | Olivan Bescos | ...... | G06T 3/0006 382/133 |
| 2010/0296806 A1* | 11/2010 | Seo | ........................ | G03B 7/003 396/236 |
| 2012/0002782 A1 | 1/2012 | Yoshida et al. | | |
| 2014/0098142 A1* | 4/2014 | Lee | ..................... | G06F 3/04845 345/676 |
| 2014/0099031 A1* | 4/2014 | Brandt | ............... | G06K 9/00228 382/201 |
| 2014/0146076 A1 | 5/2014 | Kim et al. | | |

FOREIGN PATENT DOCUMENTS

| | | | | |
|---|---|---|---|---|
| JP | | 4540123 B2 | 9/2010 | |
| JP | | 2014-106980 A | 6/2014 | |
| WO | | 2007/069141 A1 | 6/2007 | |
| WO | WO | 2007069141 A1 * | 6/2007 | ............. G06T 11/60 |
| WO | | 2010101208 A1 | 9/2010 | |

OTHER PUBLICATIONS

Communication dated Jan. 13, 2016 from the German Patent and Trademark Office issued in corresponding Application No. 102015111556.5.

* cited by examiner

CURVED LINE CORRECTION APPARATUS, METHOD, AND MEDIUM

CROSS-REFERENCE TO RELATED APPLICATIONS

The present application claims priority under 35 U.S.C. § 119 to Japanese Patent Application No. 2014-156625 filed on Jul. 31, 2014. The above application is hereby expressly incorporated by reference, in its entirety, into the present application.

BACKGROUND OF THE INVENTION

Field of the Invention

The present invention relates to a curved line correction apparatus, method, and program for correcting a curved line composed of a plurality of arranged points by moving any selected point.

Description of the Related Art

Heretofore, it has been practiced, in the medical field, to automatically extract a region of an organ, such as a heart, in a medical image and to display, for example, a contour of a left ventricular region for diagnosis and measurement of the heart.

As there may be a case where a contour of a region is not extracted correctly by the automatic extraction processing alone using a computer, for example, Japanese Patent No. 4540123 proposes a method, when a point on a curved line that forms a contour is selected by a user and the selected point is moved by the user, to correct a contour by moving a point group such that the vicinity of the selected point forms a spline curve.

Also, Japanese Unexamined Patent Publication No. 2005-028051 proposes a contour correction method by moving a point selected by the user, and Japanese Unexamined Patent Publication No. 2014-106980 proposes a contour correction method in which a contour is corrected toward the outside if the point specified by the user is on the outside of the contour, while if the point specified by the user is on the inside of the contour, the contour is corrected toward the inside.

SUMMARY OF THE INVENTION

Figure 11:
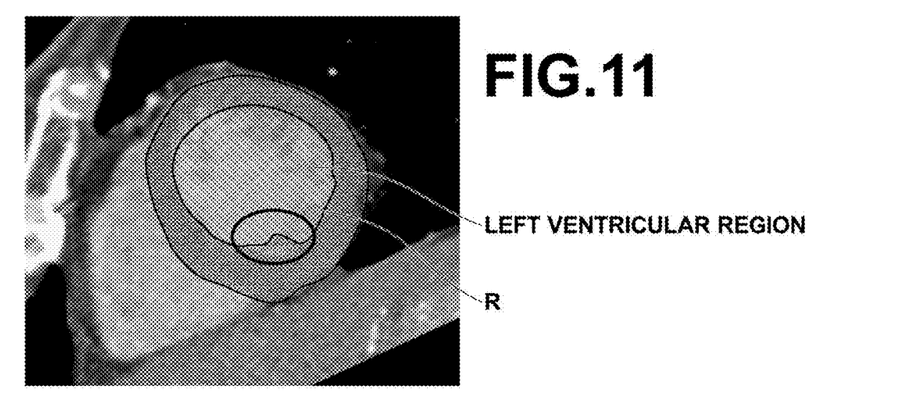
FIG. 11 shows an example of a contour of a left ventricular region extracted from a medical image of a heart.

Here, for example, considering the case where a contour range indicated by the ellipse on a contour R of a left ventricular region shown in FIG. 11 is to be corrected. In this case, a correction target point may be selected, for example, by placing a mouse pointer C on the contour R by a mouse operation as shown in FIG. 12, then a point group in a correction target range indicated by a rectangle may be moved by moving the selected correction target point, whereby the contour in the correction target range may be corrected.

Figure 12:
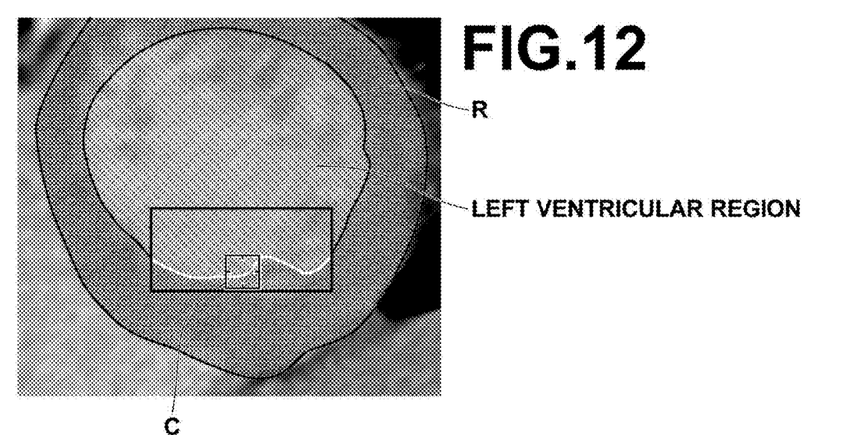
FIG. 12 shows an example in which the size of the correction target range is fixed.
Figure 13:
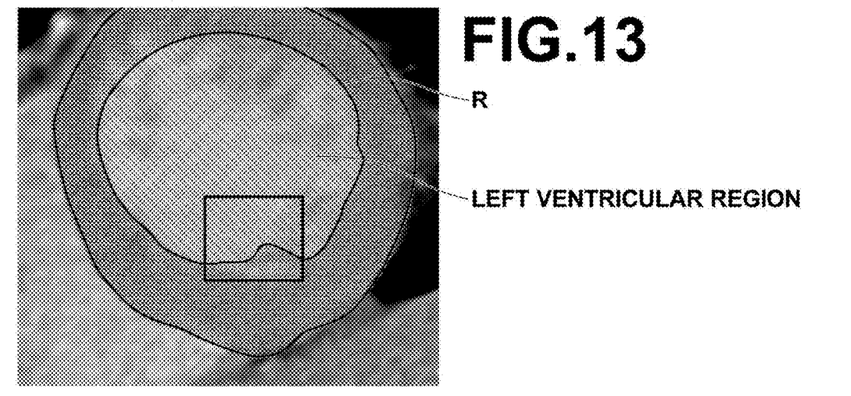
FIG. 13 shows the range of the contour actually desired to be corrected.
Figure 14:
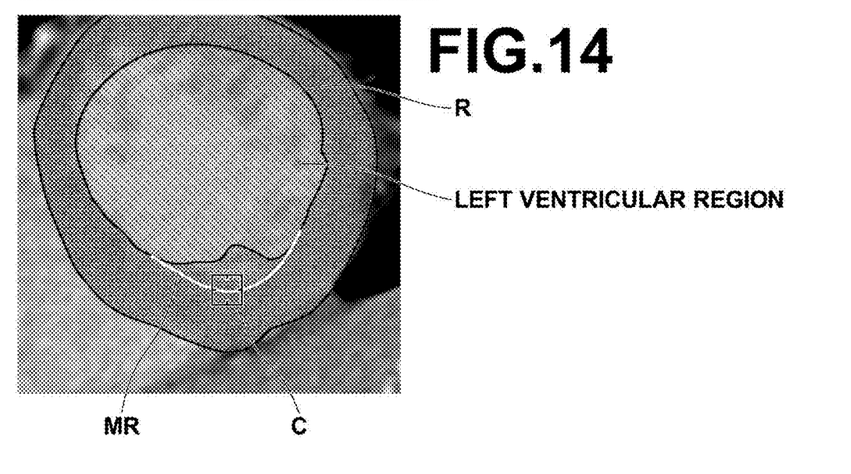
FIG. 14 shows an example in which the contour is corrected unduly.

If the correction target range indicated by the rectangle in FIG. 12 is a preset fixed range, however, even when a contour portion in a narrow range like that indicated by the rectangle in FIG. 13 is actually desired to be corrected, a contour portion in the preset correction target range which is wider than the narrow range is corrected, thereby resulting in that the corrected contour MR is corrected too extensively, as illustrated in FIG. 14. Thus, the single correction cannot bring the contour close to the image information of the actual left ventricular region and it is necessary to perform the contour correction may times.

Therefore, it is conceivable to make the correction target range changeable, instead of the preset fixed range. As a method for changing the correction target range, for example, it is conceivable to display a controller, such as a slider, on a screen and the correction target range is changed by operating of the controller with a mouse. But, such a changing method needs to move the mouse pointer in two steps: for selecting a correction target point described above; and for changing the correction target range. Thus, it is difficult to select a correction target point and to change the correction target range by a sequence of operations. Therefore, in a case, for example, where the contour correction is performed a plurality of times, it is necessary to move the mouse pointer many times, and also the viewpoint of the user is moved many times, thereby causing the contour correction to be troublesome work.

Japanese Patent No. 4540123, Japanese Unexamined Patent Publication No. 2005-028051, and Japanese Unexamined Patent Publication No. 2014-106980 propose no specific method for selecting a correction target point and changing a correction target range by a sequence of operations.

In view of the circumstances described above, it is an object of the present invention to provide a curved line correction apparatus, method, and program capable of, when a correction target point on a curved line is selected and the curved line is corrected by moving the correction target point, selecting a correction target point and changing a correction target range by a sequence of operations, thereby correcting the curved line simply and efficiently.

A curved line correction apparatus of the present invention includes a correction target point receiving unit that receives a correction target point when an instruction mark is placed on an arbitrary point on a curved line composed of a plurality of arranged points displayed on a display unit, a correction target range setting unit that sets a certain range of the curved line, including the correction target point, as a correction target range, and a correction unit that corrects a portion of the curved line within the correction target range by moving the correction target point and a point within the correction target range when movement of the instruction mark is received, wherein the correction target range setting unit changes the size of the correction target range when an instruction input to change the range is received with the instruction mark being placed on the correction target point.

The curved line correction apparatus of the present invention described above may include a display control unit that displays information representing the correction target range on the display unit.

The display control unit may display the information representing the correction target range by displaying the portion of the curved line within the correction target range and the curved line other than the portion of the curved line in different display modes.

Further, the display control unit may display the information representing the correction target range by highlighting the portion of the curved line within the correction target range.

In a case where the correction target range is a point group range within a circle centered on the correction target point, the correction target range setting unit may change the radius of the circle.

In a case where the correction target range is a point group range within a distance from the correction target point set along the curved line, the correction target range setting unit may change the distance.

In a case where, when the central point of a circular arc is taken as the correction target point, the correction target range is a point group range on the curved line included in a central angle of the circular arc, the correction target range setting unit may change the central angle of the circular arc.

The instruction mark may be moved by an input from a mouse, and the correction target range may be changed by an input of a mouse wheel, a keyboard, or a mouse click.

The curved line may represents a contour of an organ.

The correction target point receiving unit may receive selection of the correction target point when the instruction mark is placed on the arbitrary point on the curved line by a user.

A curved line correction method of the present invention includes the steps of receiving a correction target point when an instruction mark is placed on an arbitrary point on a curved line composed of a plurality of arranged points displayed on a display unit, setting a certain range of the curved line, including the correction target point, as a correction target range, and correcting a portion of the curved line within the correction target range by moving the correction target point and a point within the correction target range when movement of the instruction mark is received, wherein the size of the correction target range is changed when an instruction input to change the range is received with the instruction mark being placed on the correction target point.

A curved line correction program of the present invention causes a computer to function as a correction target point receiving unit that receives a correction target point when an instruction mark is placed on an arbitrary point on a curved line composed of a plurality of arranged points displayed on a display unit, a correction target range setting unit that sets a certain range of the curved line, including the correction target point, as a correction target range, and a correction unit that corrects a portion of the curved line within the correction target range by moving the correction target point and a point within the correction target range when movement of the instruction mark is received, wherein the correction target range setting unit changes the size of the correction target range when an instruction input to change the range is received with the instruction mark being placed on the correction target point.

According to the curved line correction apparatus, method, and program of the present invention, when a correction target point with an instruction mark being placed thereon is moved to correct a portion of the curved line within a correction target range by moving the correction target point and a point within the correction target range, an instruction input to change the range is received with the instruction mark being placed on the correction target point and this causes the size of the correction target range to be changed. This allows for selecting the correction target point and changing the correction target range by a sequence of operations, whereby the curved line may be corrected simply and efficiently.

DETAILED DESCRIPTION OF THE PREFERRED EMBODIMENTS

Figure 1:
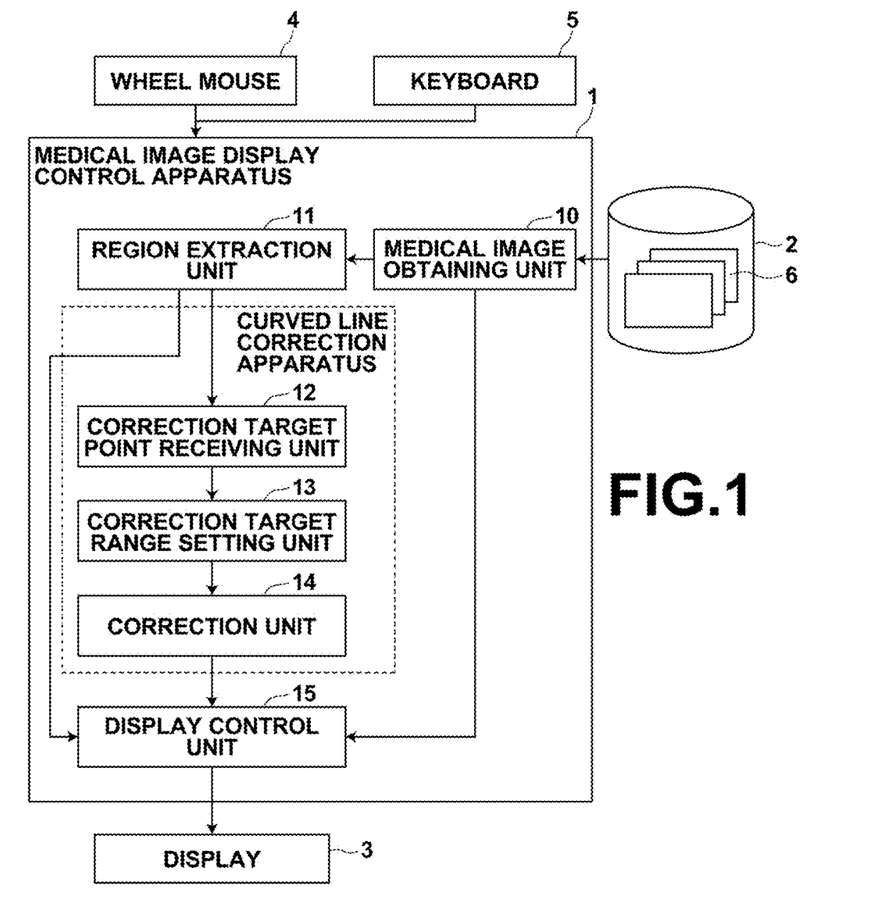
FIG. 1 is a block diagram of a medical image diagnosis support system that uses one embodiment of the curved line correction apparatus, method, and program of the present invention, illustrating the schematic configuration thereof.

Hereinafter, a medical image diagnosis support system that uses one embodiment of the curved line correction apparatus, method, and program of the present invention will be described in detail with reference to the accompanying drawings. FIG. 1 is a block diagram of the medical image diagnosis support system of the present embodiment.

As illustrated in FIG. 1, the medical image diagnosis support system of the present embodiment includes a medical image display control apparatus 1, a medical image storage server 2, a display 3, a wheel mouse 4, and a keyboard 5.

The medical image display control apparatus 1 is configured by installing a curved line correction program of the present embodiment on a computer.

The medical image display control apparatus 1 includes a central processing unit (CPU) and storage devices, such as for example a semiconductor memory, a hard disk, and a solid state drive (SSD). The storage device includes the curved line correction program of the present embodiment, and execution of the curved line correction program by the central processing unit causes a correction target point receiving unit 12, a correction target range setting unit 13, and a correction unit 14 shown in FIG. 1 to be operated. In the present embodiment, the correction target point receiving unit 12, the correction target range setting unit 13, and the correction unit 14 constitute a curved line correction apparatus of the present invention.

The medical image display control apparatus 1 includes a medical image obtaining unit 10, a region extraction unit 11, and a display control unit 15, other than the curved line correction apparatus of the present invention. Each of these units is configured when a predetermined program is installed and operates when the program is executed by the central processing unit.

The medical image obtaining unit 10 obtains a medical image 6 of a patient captured in advance. The medical image 6 may be, for example, a tomographic image captured by a computed tomography (CT) system, a magnetic resonance imaging (MRI) system, or the like, or a three-dimensional image composed of a plurality of tomographic images. The tomographic images may include axial cross-sectional images, sagittal cross-sectional images, coronal cross-sectional images, and other multi-planar reconstruction (MPR) cross-sectional images.

The medical image 6 is stored in the medical image storage server 2 in advance with patient identification information and, based on patient identification information inputted by the user using the keyboard 5 or the like, the medical image obtaining unit 10 reads out a medical image 6 having the patient identification information from the medical image storage server 2.

The region extraction unit 11 extracts a predetermined region from the medical image 6 obtained by the medical image obtaining unit 10. More specifically, the region extraction unit 11 of the present embodiment obtains a three-dimensional image composed of a plurality of tomographic images obtained by imaging a heart, as the medical image 6, and extracts a left ventricular region of the heart and a myocardial region surrounding the ventricular region from the three-dimensional image. Any known method may be used for extracting the left ventricular region and the myocardial region. Information of the left ventricular region and the myocardial region extracted by the region extraction unit 11 is outputted to the display control unit 15 and displayed on the display 3 by the display control unit 15 with a tomographic image of the heart.

The present embodiment obtains a three-dimensional image of a heart and extracts a left ventricular region and a myocardial region of the heart, as described above, but not limited to this and other organ regions, such as a lung region, a liver region, or a blood vessel region, bone regions, and lesion regions, such as a tumor may be extracted.

The correction target point receiving unit 12 receives selection of an arbitrary point on a curved line that forms a contour of the left ventricular region extracted by the region extraction unit 11, thereby accepting the selection of a correction target point. The curved line that forms the contour of the left ventricular region is composed of a plurality of arranged points and a correction target point is selected when one of the plurality of points is selected by the user on the display 3.

The correction target point is selected when a mouse pointer (corresponding to the instruction mark) displayed on the display is placed on an arbitrary point on the curved line by the user using the wheel mouse 4. The mouse pointer may be displayed in different display modes between a case where the mouse pointer is located on the curved line that forms the contour of the left ventricular region or in the vicinity thereof and a case where the mouse pointer is neither located on the curved line that forms the contour of the left ventricular region nor in the vicinity thereof. For example, if the mouse pointer is located on the curved line that forms the contour of the left ventricular region or in the vicinity thereof, it may be displayed as a cross shaped cursor or a rectangular shaped cursor to facilitate selection of a correction target point while if the mouse pointer is located neither on the curved line that forms the contour of the left ventricular region nor in the vicinity thereof, it may be displayed as an arrow mark.

In the present embodiment, the correction target point is manually selected by the user as described above, but the correction target point may be extracted automatically. For example, a contour portion that requires correction may be extracted using learning and one point in the contour portion may be determined as the correction target point. In this case, the mouse pointer automatically moves onto the automatically extracted correction target point.

The correction target range setting unit 13 sets a range of a contour portion that includes the correction target point selected by the user as the correction target range. The correction target range is a range of point group which, when the correction target point is moved by the user through a mouse operation, is moved with the correction target point, and the contour within the correction target range is corrected by the movement of the correction target point and the point group.

The correction target range setting unit 13 of the present embodiment sets a predetermined point group range as the correction target range at the time when a given correction point is selected by the user. Then, if an instruction input to change the correction target range is given with the correction target point being selected as described above, that is, with the mouse pointer being placed on the correction target point, the correction target range setting unit 13 receives the instruction input and changes the size of the correction target range according to the instruction input.

More specifically, the correction target range setting unit 13 of the present embodiment receives a mouse wheel operation by the user, with the mouse pointer being placed on the correction target point, and changes the size of the correction target range according to the direction and the amount of the rotation. For example, if a rotation operation of the mouse wheel in one direction is received, a change is made such that the greater the amount of rotation, the greater the size of the correction target range, while if a rotation operation of the mouse wheel in the other direction is received, a change is made such that the greater the amount of rotation, the smaller the size of the correction target range.

In the present embodiment, an instruction input to change the correction target range is made with the mouse wheel, but not limited to this and, for example, an instruction input to change the correction target range may be made using the keyboard 5 or by a mouse-click operation. In the case where the instruction input is made using the keyboard, the correction target range may be changed according to the direction and pressing count or time of the arrow key (direction key) of the keyboard 5. In the case where the instruction input is made by a mouse-click operation, the correction target range may be changed such that, for example, if the right mouse button is clicked, the correction target range is increased according to the number of clicks, while if the left mouse button is clicked, the correction target range is decreased according to the number of clicks.

When the mouse pointer is moved by the user through a mouse operation after the correction target point is selected by the user, the correction unit 14 moves the correction target point by receiving the movement of the mouse pointer and moves the point group in the correction target range according to the movement, thereby correcting the curved line in the correction target range.

As for the movement of the point group in the correction target range, the point group in the correction target range may be moved such that, for example, the correction target point and a point outside the correction target range is connected smoothly by a spline curve. Any known method may be used for such a spline curve contour correction.

The display control unit 15 displays the medical image 6 obtained by the medical image obtaining unit 10, the region and the contour thereof extracted by the region extraction unit 11, the mouse pointer, and the like, on the display 3. The display control unit 15 of the present embodiment also displays, when the correction target range is set or changed by the correction target range setting unit 13, information representing the correction target range.

More specifically, the display control unit 15 of the present embodiment displays the information representing the correction target range by displaying a contour portion within the correction target range and the contour outside the correction target range in different display modes. For example, the contour portion within the correction target range is enhance-displayed by highlighting. But, the display method of the contour portion within the correction target range is not limited to this and, for example, the contour portion within the correction target range may be blink-displayed or only the points at both ends of the contour portion of within the correction target range may be displayed in a different color or brightness.

Next, an operation of the medical image diagnosis support system of the present embodiment will be described with reference to the flowchart shown in FIG. 2. As the medical image diagnosis support system of the present embodiment is characterized by the operation of the foregoing curved line correction apparatus, the description will be made focusing on that point.

First, a medical image 6 is read out and obtained by the medical image obtaining unit 10 from the medical image storage server 2 based on a user input of patient identification information and the like (S10).

The medical image 6 obtained by the medical image obtaining unit 10 is outputted to the display control unit 15 and displayed on the display 3, as well as being outputted to the region extraction unit 11. Then, a left ventricular region and a myocardial region are extracted by the region extraction unit 11 (S12), and information of the left ventricular region and the myocardial region is outputted to the display control unit 15. Based on the information of the left ventricular region and the myocardial region, the display control unit 15 displays the left ventricular region and the myocardial region and contours of these regions on the display 3 (S14).

Figure 3:
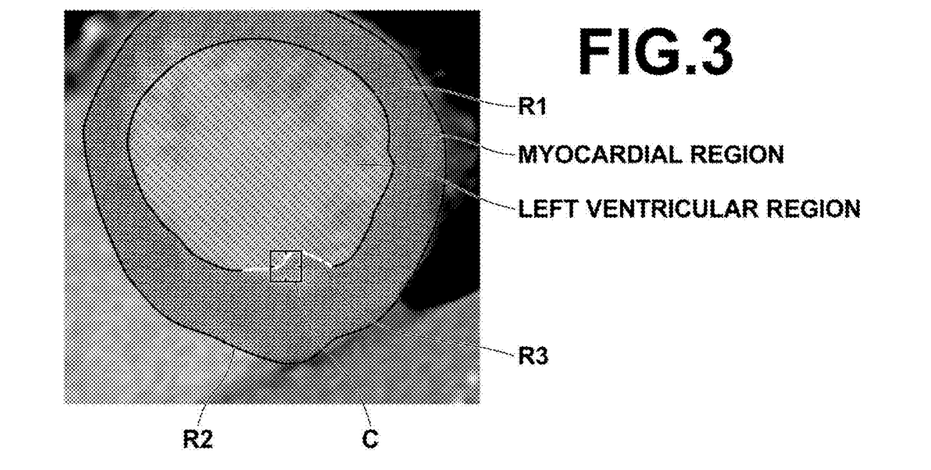
FIG. 3 shows an example in which a tomographic image of a heart, a left ventricular region of the heart and its contour R1, a myocardial region and its contour R2, and a mouse pointer C are displayed on the display 3.

Next, in a case where the contour of the left ventricular region displayed on the display 3 does not correspond to the image of the actual left ventricular region and the user desires to correct the contour, the mouse pointer is moved to where the correction is desired to be made by operating the wheel mouse 4 and a correction target point is selected by placing the mouse pointer on the contour of the left ventricular region. Then, the selection information of the correction target point is received by the correction target point receiving unit 12 (S16). FIG. 3 shows an example in which a tomographic image of a heart, a left ventricular region of the heart and its contour R1, a myocardial region and its contour R2, and a mouse pointer C are displayed on the display 3. FIG. 3 shows the state in which the mouse pointer C is placed on the contour R1 of the left ventricular region and a correction target point is selected. The contour R1 is indicated by a line in FIG. 3 but, in actuality, the contour is composed of a plurality of arranged points, as illustrated in FIG. 4, and placing the mouse pointer C on an arbitrary point P of the plurality of points results in that the point P is selected as the correction target point.

Figure 4:
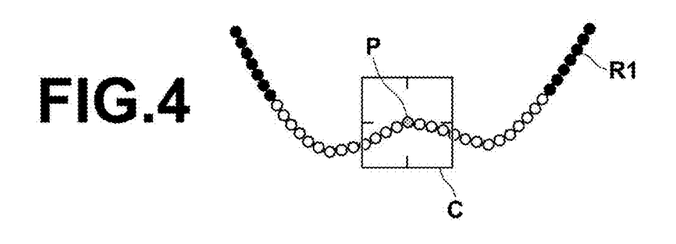
FIG. 4 is a drawing for explaining selection of a correction target point.

Then, when the correction target point is selected, as illustrated in FIGS. 3 and 4, a point group range, which includes the correction target point, on the contour is set as the correction target range by the correction target range setting unit 13. As described above, at the time when a given correction target point is selected, a predetermined range is set as the correction target range. Then, when the correction target range is set, a contour portion R3 within the correction target range is highlighted, as shown in FIGS. 3 and 4.

Figure 5:
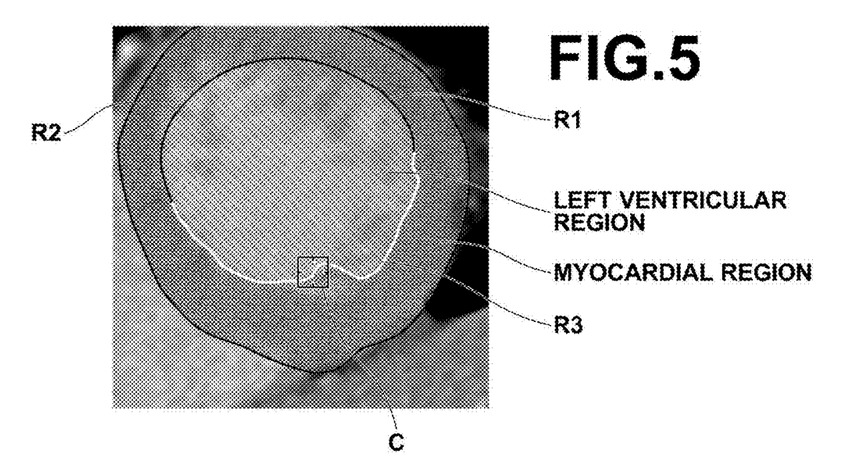
FIG. 5 shows an example in which the correction target range is increased.

Next, if the user wants to change the correction target range from the preset range, the user inputs a change instruction to change the correction target range by rotation operating the wheel of the wheel mouse 4, with the mouse pointer being placed on the correction target point. If the change instruction to change the correction target range is inputted by the user (S18: YES), the correction target range setting unit 13 increases or decreases the correction target range according to the change instruction. FIG. 5 shows an example of a case where the correction target range is changed so as to be greater than the correction target range set in FIG. 3. As illustrated in FIG. 5, the range of the highlighted contour R3 is increased.

Figure 6:
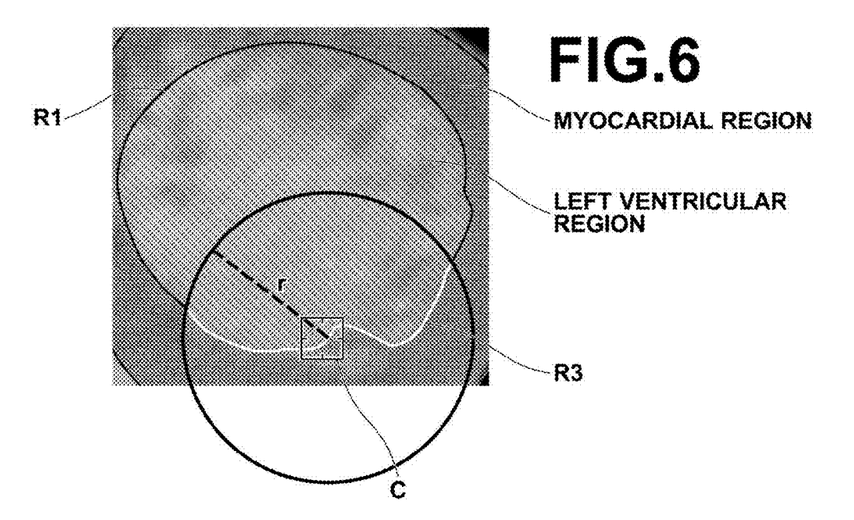
FIG. 6 shows an example in which a point group range in a circle of radius r centered on the correction target point is taken as the correction target range.

Now, the method for changing the correction target range will be described in more detail. The correction target range is set, for example, as a point group range in a circle of radius r centered on the correction target point, as illustrated in FIG. 6. In this case, the correction target range is changed by changing the radius r of the circle described above.

Figure 7:
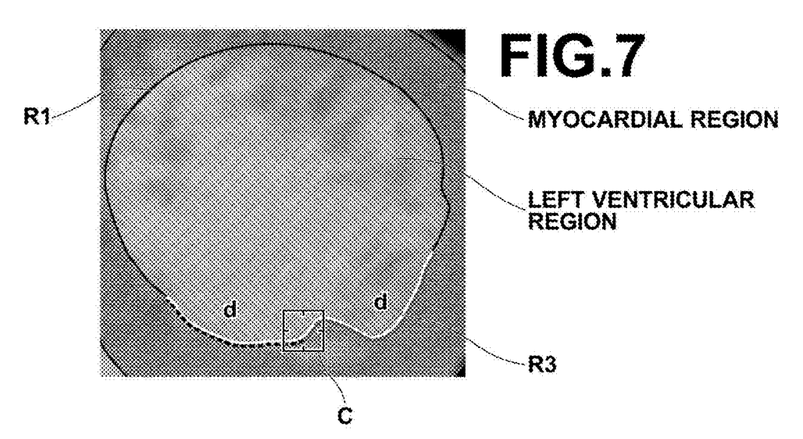
FIG. 7 shows an example in which a point group range in a distance d from the correction target point along the contour is taken as the correction target range.

The correction target range may be set as a point group range in a distance d from the correction target point along the contour, as illustrated in FIG. 7. In this case, the correction target range is changed by changing the distance d described above. In FIG. 7, point group ranges in the same distance d on both sides of the correction target point are taken as the correction target range but not necessarily in the same distance on both sides, and the distance on one side may be different from the distance on the other side, or each distance may be allowed to be changed separately and independently. As a method for changing the distances separately, for example, the distance on one side may be determined by an initial mouse wheel operation and, after it is detected that no mouse wheel operation has been detected for a certain time, the distance on the other side may be determined by the next mouse wheel operation.

Figure 8:
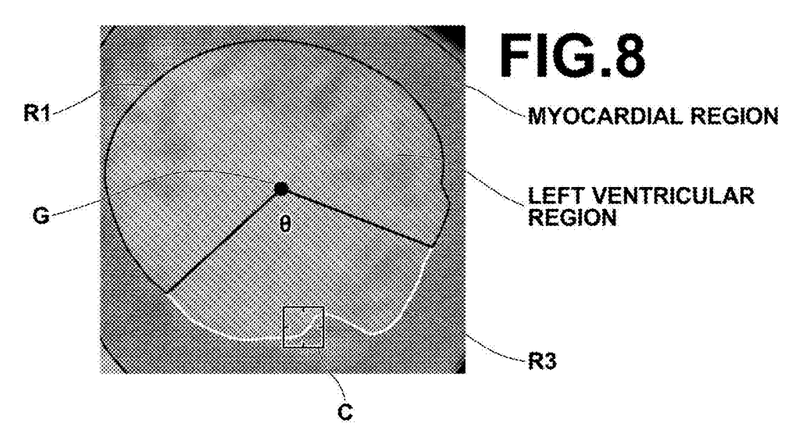
FIG. 8 shows an example in which, when the central point of a circular arc centered on the center of gravity G of a left ventricular region is taken as the correction target point, a point group range on the contour included in the range of a central angle $\theta$ is taken as the correction target range.

Further, when the central point of a circular arc centered on the center of gravity G of the extracted left ventricular region is taken as the correction target point, the correction target range may be set as a point group range on the contour included in the range of a central angle θ of the circular arc, as illustrated in FIG. 8. In this case, a change is made by changing the central angle θ.

In a case where the contour correction target range includes a smooth portion and a finely changing unevenness (jagged) portion, the method that sets radius r or central angle θ, among the methods described above, allows the operator to set ranges which are intuitively considered to be equal to each other.

Figure 2:
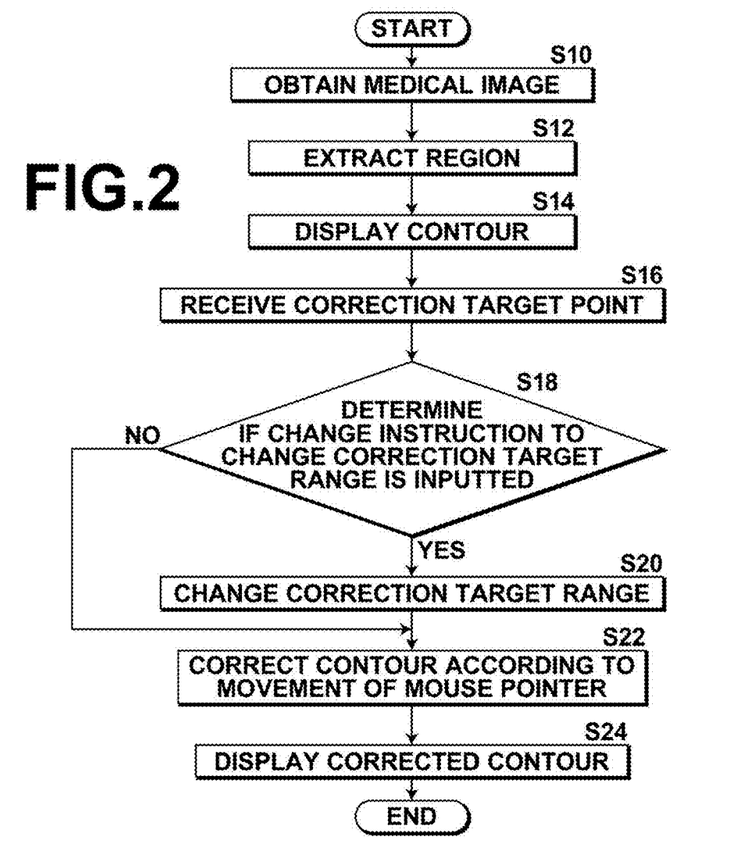
FIG. 2 is a flowchart for explaining the operation of the medical image diagnosis support system that uses one embodiment of the curved line correction apparatus, method, and program of the present invention.

Returning to the step S18 in FIG. 2, if a change instruction to change the correction target range is given by the user, the correction target range setting unit 13 changes the correction target range according to the change instruction (S20).

Figure 9:
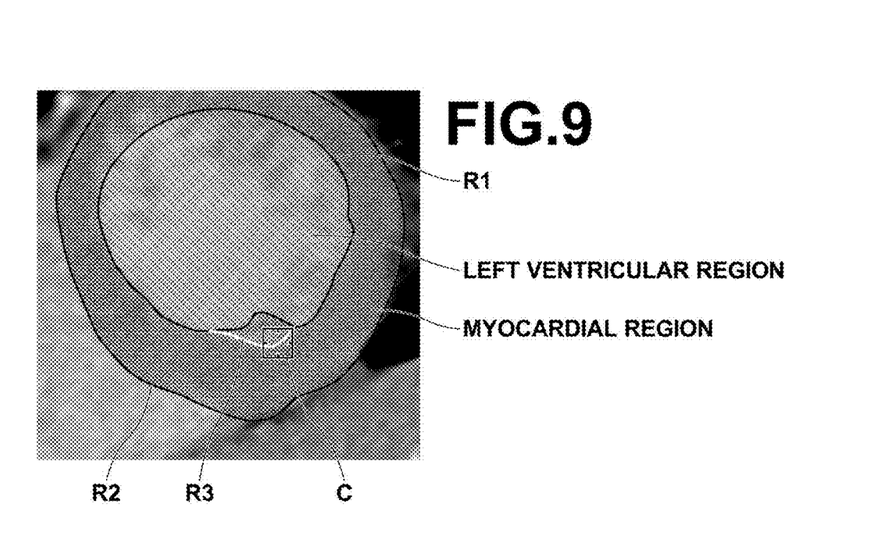
FIG. 9 shows an example of a corrected contour.
Figure 10:
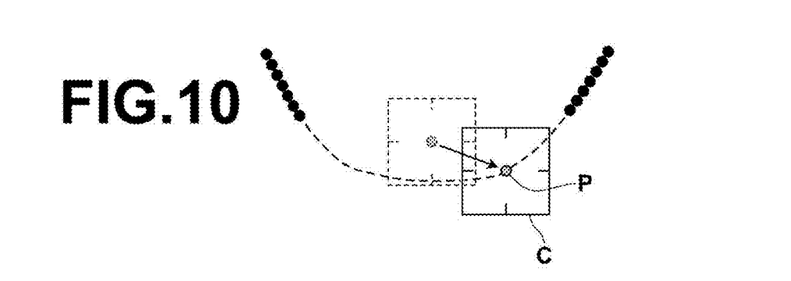
FIG. 10 is a drawing for explaining an example in which the point group constituting a contour is increased or decreased along with the correction of the contour.

After the correction target range is changed, the user moves the mouse pointer by moving the mouse, and the correction unit 14 moves the correction target point by receiving the movement of the mouse pointer and further moves the point group within the correction target range according to the movement of the correction target point, thereby correcting the curved line within the correction target range (S22). Then, the display control unit 15 displays the contour corrected by the correction unit 14 on the display 3 (S24). FIG. 9 shows an example of a corrected contour R3. For example, in a case where the correction target point P is moved as illustrated in FIG. 10, the length of the contour from the correction target point P to the points outside the correction target range (length of the dotted line in FIG. 10) may possibly differ before and after the correction. In that case, if the length of the contour from the correction target point P to the points outside the correction target range is increased, the number of points that form the contour may be increased by that amount, while if the length of the contour is decreased, the number of points that form the contour may be decreased by that amount.

In the foregoing embodiment, the correction target range is changed with the mouse pointer being placed on the correction target point, but if a wheel operation is performed by the user without the mouse pointer being placed on the correction target point, a generally known ordinary operation may be performed, such as paging of images, scaling, and the like.

In the foregoing description, when a correction target point is moved, a point group within the correction target range is moved such that the correction target point and a point outside the correction target range are connected by a spline curve, but not limited to this and, for example, an arrangement may be adopted in which contour extraction processing using an active contour model, such as SNAKES, is performed on a tomographic image and the point group within the correction target range is moved so as to be fitted to the re-extracted contour. For example, in a case where a left ventricular region is extracted from a three-dimensional image, as in the foregoing embodiment, the contour of the left ventricular region to be extracted at a given tomographic image may sometimes be influenced by the contour of the left ventricular region extracted at a tomographic image adjacent to the given tomographic image. Here, the re-extraction of a contour in a tomographic image and the fitting performed in the manner described above allow the contour to be better matched with the image information of the left ventricular region.

In the foregoing, the description has been made of a case in which a contour extracted from a medical image is corrected, but the correction target curved line of the present invention is not limited to a contour extracted from a medical image and the present invention is also applicable to correcting a curved line in an image in technical fields other than the medical field.

What is claimed is:

1. A curved line correction apparatus, comprising a memory storing computer executable instructions and a processor configured to execute the stored instructions, which when executed by the processor cause the processor to perform the following operations:
    receive a correction target point when an instruction mark is placed on an arbitrary point on a curved line composed of a plurality of arranged points displayed on a display unit;
    set a certain range of the curved line, including the correction target point, as a correction target range;
    correct a portion of the curved line within the correction target range by moving the correction target point and a point within the correction target range when movement of the instruction mark is received; and
    change the size of the correction target range when an instruction input to change the range is received with the instruction mark being placed on the correction target point, the instruction input being based on a user's action on an input device and being received before receiving the movement of the instruction mark,
    wherein the correction target range is a point group range on the curved line included in a range defined by a central angle of a circular arc formed by taking the correction target point as a central point thereof, and the processor changes the size of the correction target range by changing the central angle of the circular arc.

2. The curved line correction apparatus of claim 1, wherein the processor is further caused to display information representing the correction target range on the display unit.

3. The curved line correction apparatus of claim 2, wherein the processor is further caused to display the information representing the correction target range by displaying the portion of the curved line within the correction target range and the curved line other than the portion of the curved line in different display modes.

4. The curved line correction apparatus of claim 3, wherein the processor is further caused to display the information representing the correction target range by highlighting the portion of the curved line within the correction target range.

5. The curved line correction apparatus of claim 1, wherein:
    the correction target range is the point group range within a circle centered on the correction target point; and
    the processor is further configured to change the radius of the circle.

6. The curved line correction apparatus of claim 1, wherein:
    the correction target range is the point group range within a distance from the correction target point set along the curved line; and
    the processor is caused to change the distance.

7. The curved line correction apparatus of claim 1, wherein
    the central point of the circular arc is taken as the correction target point.

8. The curved line correction apparatus of claim 1, wherein
    the instruction mark is moved by an input from a mouse.

9. The curved line correction apparatus of claim 1, wherein the curved line represents a contour of an organ.

10. The curved line correction apparatus of claim 1, wherein processor is further caused to receive selection of the correction target point when the instruction mark is placed on the arbitrary point on the curved line by a user.

11. The curved line correction apparatus of claim 1, wherein the input device comprises at least one of a mouse and a keyboard.

12. The curved line correction apparatus of claim 1, wherein the user's action on the input device comprises at least one of:
    rotation operation of a mouse wheel, and
    operation of a keyboard, wherein the range is increased by operating a first key and the range is decreased by operating a second key.

13. A curved line correction method, comprising:
    receiving a correction target point when an instruction mark is placed on an arbitrary point on a curved line composed of a plurality of arranged points displayed on a display unit;

setting a certain range of the curved line, including the correction target point, as a correction target range; and correcting a portion of the curved line within the correction target range by moving the correction target point and a point within the correction target range when movement of the instruction mark is received, wherein the size of the correction target range is changed when an instruction input to change the range is received with the instruction mark being placed on the correction target point, the instruction input being based on a user's action on an input device and being received before receiving the movement of the instruction mark, wherein the correction target range is a point group range on the curved line included in a range defined by a central angle of a circular arc formed by taking the correction target point as a central point thereof, and the processor changes the size of the correction target range by changing the central angle of the circular arc.

14. The curved line correction method of claim 13, wherein the user's action on the input device comprises at least one of:

rotation operation of a mouse wheel, and operation of a keyboard, wherein the range is increased by operating a first key and the range is decreased by operating a second key.

15. A non-transitory computer-readable recording medium containing a curved line correction program for causing a computer to perform the following functions:

receive a correction target point when an instruction mark is placed on an arbitrary point on a curved line composed of a plurality of arranged points displayed on a display unit;

set a certain range of the curved line, including the correction target point, as a correction target range;

correct a portion of the curved line within the correction target range by moving the correction target point and a point within the correction target range when movement of the instruction mark is received; and change the size of the correction target range when an instruction input to change the range is received with the instruction mark being placed on the correction target point, the instruction input being based on a user's action on an input device and being received before receiving the movement of the instruction mark, wherein the correction target range is a point group range on the curved line included in a range defined by a central angle of a circular arc formed by taking the correction target point as a central point thereof, and the processor changes the size of the correction target range by changing the central angle of the circular arc.

16. The non-transitory computer readable recording medium containing the curved line correction program of claim 15, wherein the user's action on the input device comprises at least one of:

rotation operation of a mouse wheel, and operation of a keyboard, wherein the range is increased by operating a first key and the range is decreased by operating a second key.

* * * * *